(12) United States Patent
Eberler et al.

(10) Patent No.: US 12,189,006 B2
(45) Date of Patent: Jan. 7, 2025

(54) GANTRY TUBE FOR MEDICAL IMAGING SYSTEM

(71) Applicant: Siemens Medical Solutions USA, Inc., Malvern, PA (US)

(72) Inventors: Ludwig Eberler, Neumarkt i.d.OPf. (DE); James L. Corbeil, Knoxville, TN (US); Martin Schramm, Eckental (DE); Stefan Stocker, Großenseebach (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 114 days.

(21) Appl. No.: 18/040,491

(22) PCT Filed: Aug. 23, 2021

(86) PCT No.: PCT/US2021/071250
§ 371 (c)(1),
(2) Date: Feb. 3, 2023

(87) PCT Pub. No.: WO2022/076957
PCT Pub. Date: Apr. 14, 2022

(65) Prior Publication Data
US 2023/0305085 A1    Sep. 28, 2023

Related U.S. Application Data

(60) Provisional application No. 63/198,285, filed on Oct. 8, 2020.

(51) Int. Cl.
*G01R 33/28* (2006.01)
*A61B 6/00* (2006.01)
*A61B 6/03* (2006.01)

(52) U.S. Cl.
CPC .............. *G01R 33/28* (2013.01); *A61B 6/037* (2013.01); *A61B 6/4417* (2013.01)

(58) Field of Classification Search
CPC ....... G01R 33/28; A61B 6/037; A61B 6/4417; A61B 5/055; A61B 6/4266
See application file for complete search history.

(56) References Cited

U.S. PATENT DOCUMENTS

| | | | |
|---|---|---|---|
| 2005/0067578 A1* | 3/2005 | Ueno | G01T 1/2985 250/370.09 |
| 2008/0208035 A1 | 8/2008 | Nistler et al. | |
| 2013/0284936 A1 | 10/2013 | McBroom et al. | |

(Continued)

OTHER PUBLICATIONS

International Search Report for Corresponding PCT Application No. PCT/US2021/071250, dated Dec. 2, 2021.

*Primary Examiner* — G. M. A Hyder (57) ABSTRACT

A gantry tube for a medical imaging system. The gantry tube includes a first tube located within a second tube, wherein the first tube is oriented about a longitudinal axis of the system. The gantry tube also includes a plurality of wall elements that extend between the first and second tubes, wherein the walls and first and second tubes form a plurality of channels that extend in an axial direction substantially parallel to the longitudinal axis wherein each channel is configured to hold a detector of the system. A detector is inserted into or removed from an associated channel in an axial direction from either a first end or a second end of the gantry tube.

20 Claims, 6 Drawing Sheets

(56) References Cited

U.S. PATENT DOCUMENTS

2017/0135580 A1    5/2017  Lips et al.
2018/0095182 A1*  4/2018  Su ........................ G01T 1/2985
2018/0231673 A1*  8/2018  Yan ....................... G01T 1/2985

* cited by examiner

GANTRY TUBE FOR MEDICAL IMAGING SYSTEM

CROSS REFERENCE TO RELATED APPLICATION

This application claims the benefit under 35 U.S.C. § 119(e) of U.S. Provisional Application No. 63/198,285, filed on Oct. 8, 2020 which is incorporated herein by reference in its entirety and to which this application claims the benefit of priority.

TECHNICAL FIELD

Aspects of the present invention relate to a gantry tube for a medical imaging system, and more particularly, to a gantry tube having a plurality of wall elements that extend between first and second tubes to form channels that extend in an axial direction substantially parallel to a longitudinal axis of the system wherein a detector of the system is inserted into or removed from an associated channel in the axial direction.

BACKGROUND

A magnetic resonance/positron emission tomography (MR/PET) imaging system is a hybrid diagnostic system that includes two different imaging modalities. The integration of MR and PET imaging systems requires the location of PET detectors within a magnetic resonance imaging (MRI) system volume. Available space within an integrated MR/PET system comes at a premium of both cost and performance, with components often competing for an optimal location. For instance, a radio frequency (RF)-transmit antenna of the MRI system and the PET detectors of the PET system must both be placed as close to the patient as possible. In addition, an RF system of the MRI system and the PET electronics require electromagnetic shielding to protect each other against respective frequencies emitted by the RF system and PET detectors. As a result, a compromise solution is utilized that allows for the suitable location of the PET detectors while also allowing sufficient room for shielding and ease of access to the PET detectors during servicing or maintenance.

Figure 1:
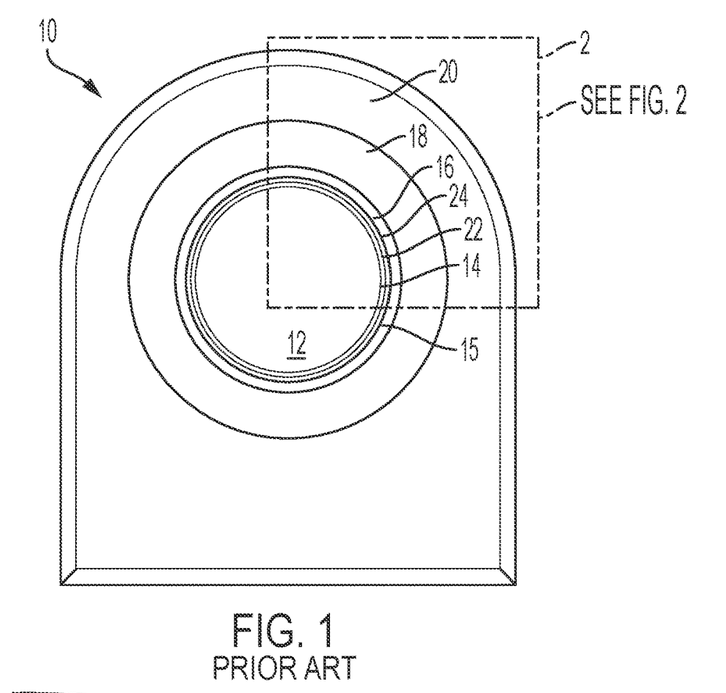
FIG. 1 is a front view of a prior art MR/PET imaging system.
Figure 2:
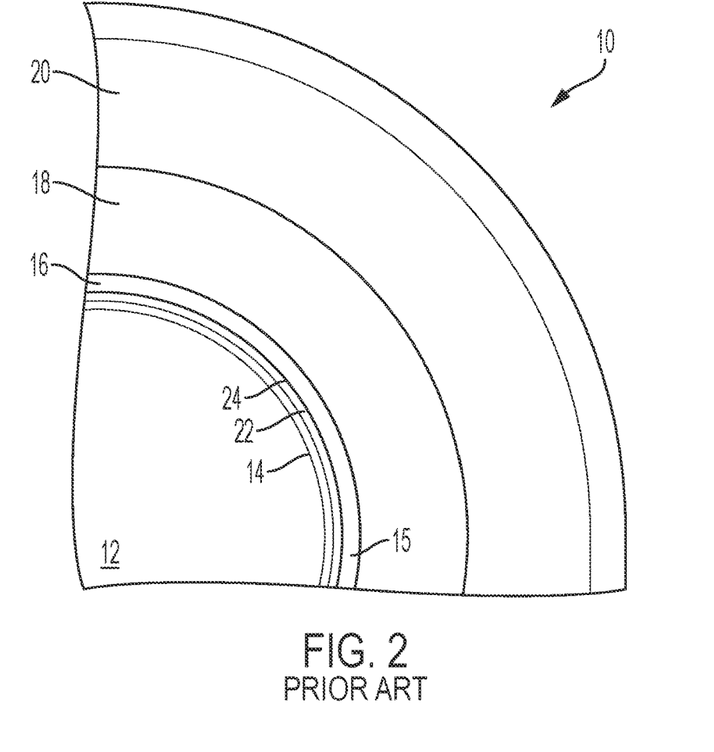
FIG. 2 is enlarged view of area 2 of FIG. 1.
Figure 3:
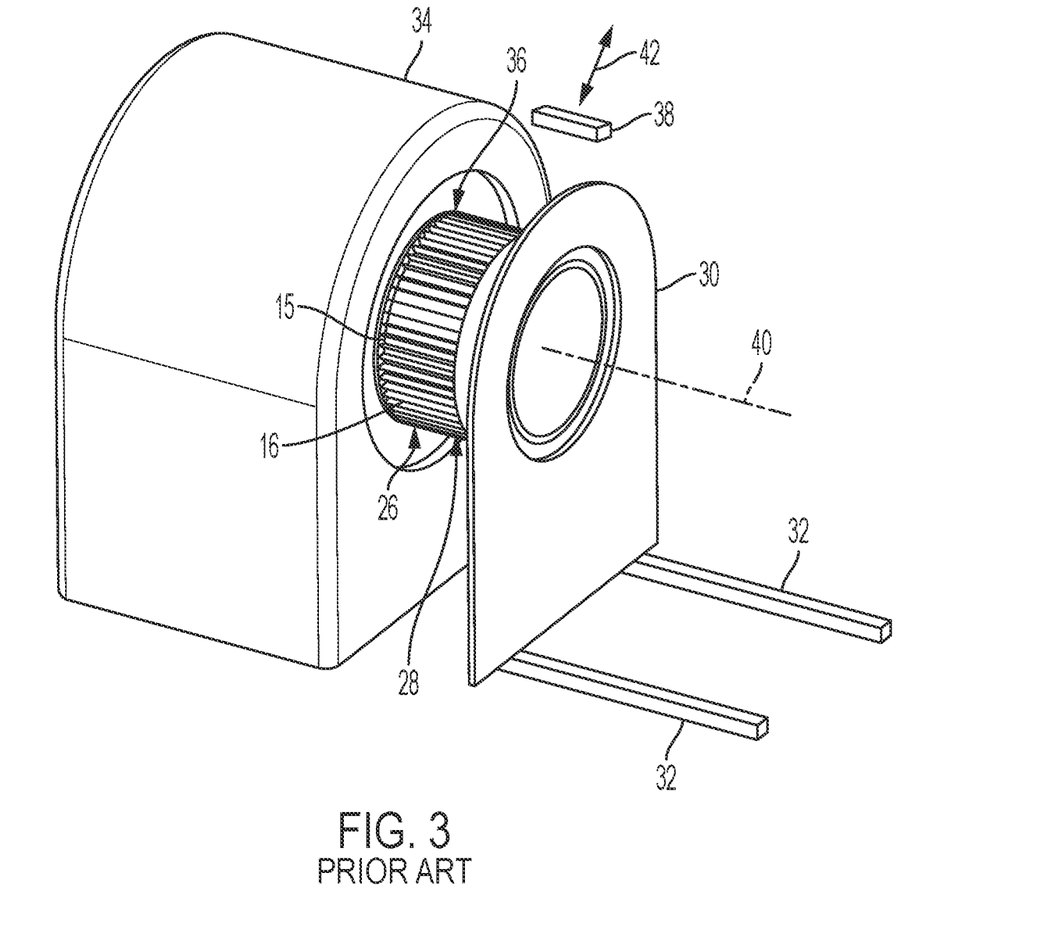
FIG. 3 is a perspective view of a prior art MR/PET imaging system wherein a PET gantry is shown in an extended position.

Referring to FIG. 1, a front view of a conventional MR/PET imaging system 10 is shown. FIG. 2 is enlarged view of area 2 of FIG. 1. The system 10 includes a patient bore 12 or tunnel that receives a patient to be scanned, RF transmit antenna or body coil 14 (component of the MRI system), PET gantry 16 (part of the PET system) that includes a gantry tube 15, gradient coil 18 (a component of the MRI system) and superconducting magnet 20 (a component of the MRI system). The PET gantry 16 includes a plurality of PET detectors and an RF screen 22 (a component of the MRI system) located on an inner surface 24 of a gantry tube 15. It would be advantageous in such systems to provide access to a single PET detector without having to disassemble or disturb substantial portions of system 10, especially if leaving the PET gantry 16 in place. The PET detectors may be located either on a separate gantry tube 15 or integrated into a RF-transmit antenna tube. In both conventional arrangements, the PET detectors are installed or loaded radially into a supporting tube. In order to gain access to the PET detectors, removal of a substantial portion of the structure from the system 10 is required even if only one PET detector needs servicing. Referring to FIG. 3, a perspective view of the system 10 is shown wherein the PET gantry 16 is in an extended position. In this position, PET detectors 26 of the system 10 are exposed thus enabling servicing of the PET detectors 26. A first end 28 of the PET gantry 16 is supported by a backplane 30 that is moveably attached to service rails 32 that enable separation of the backplane 30 from a remaining portion 34 of the system 10 and movement of the PET gantry 16 to the extended position. A second end 36 of the PET gantry 16, opposite the first end 28, stays in the remaining portion 34 and is supported by rolling elements. The gantry tube 15 is configured to hold the PET detectors 26 such that the PET detectors 26 are inserted into the gantry tube 15, or removed from the gantry tube 15 (exemplary PET detector 38 is shown in FIG. 2), in a direction substantially transverse to a longitudinal center axis 40 of the system 10 (i.e., in a radial direction) as shown by arrow 42.

SUMMARY OF THE INVENTION

A gantry tube for a medical imaging system is disclosed. The gantry tube includes a first tube located within a second tube, wherein the first tube is oriented about a longitudinal axis of the system. The gantry tube also includes a plurality of wall elements that extend between the first and second tubes, wherein the walls and first and second tubes form a plurality of channels that extend in an axial direction substantially parallel to the longitudinal axis wherein each channel is configured to hold a detector of the system. A detector is inserted into or removed from an associated channel in the axial direction from either a first end or a second end of the gantry tube.

In addition, a method of inserting a detector into a gantry tube of a medical imaging system or removing a detector is disclosed. The method includes providing a first tube located within a second tube, wherein the first tube is oriented about a longitudinal axis of the system. The method also includes providing a plurality of wall elements that extend between the first and second tubes to form a plurality of channels wherein the channels extend in an axial direction substantially parallel to the longitudinal axis. Further, the method includes moving a detector in the axial direction to either insert the detector into an associated channel or remove a detector from an associated channel.

Those skilled in the art may apply the respective features of the present invention jointly or severally in any combination or sub-combination.

BRIEF DESCRIPTION OF THE DRAWINGS

The exemplary embodiments of the invention are further described in the following detailed description in conjunction with the accompanying drawings, in which.

DETAILED DESCRIPTION

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

Figure 4:
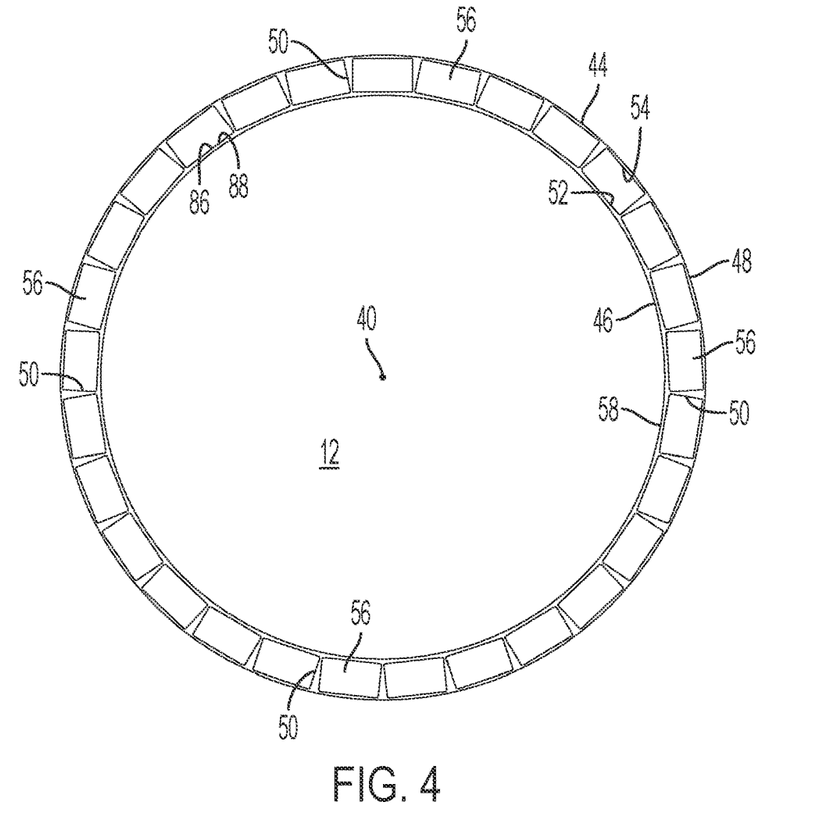
FIG. 4 is a front view of a gantry tube used to form a PET gantry in accordance with an aspect of the invention.

Referring to FIG. 4, a front view of a gantry tube 44 used to form a PET gantry in accordance with an aspect of the invention is shown. The gantry tube 44 is part of an imaging system such as a magnetic resonance/positron emission tomography (MR/PET) imaging system 90 (see FIG. 8). The gantry tube 44 includes a first tube 46 located within a second tube 48. The first tube 46 is positioned about the longitudinal axis 40. The gantry tube 44 further includes a plurality of wall elements 50 connected between the first 46 and second 48 tubes. Each wall 50 extends between an outer surface 52 of the first tube 46 and an inner surface 54 of the second tube 48 to form a plurality of channels 56 between the first 46 and second 48 tubes. In accordance with an aspect of the invention, each channel 56 holds an associated PET detector 74 of the system 90 (FIG. 8). Further, each channel 56 is configured to receive an associated PET detector 74 in an axial direction as will be described in connection with FIGS. 7A-7B.

Figure 5:
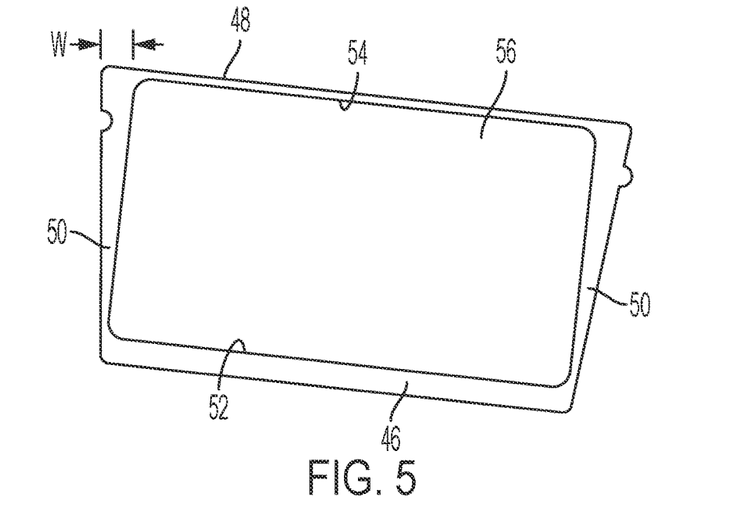
FIG. 5 depicts an enlarged view of an exemplary channel that receives a PET detector.

FIG. 5 depicts an enlarged view of an exemplary channel 56. A size or width W of each wall 50 gradually increases as the wall 50 extends from the first tube outer surface 52 toward the second tube inner surface 54 to form a substantially triangularly or wedge-shaped wall 50. This forms a channel 56 having a substantially rectangular shape suitable for receiving a single PET detector 74. Alternatively, the channel 56 may have other shapes suitable for receiving a corresponding PET detector shape such as square shape, for example. An inner surface 58 (see FIG. 4) of the first tube 46 defines the patient bore 12 that receives a patient to be scanned.

Figure 6:
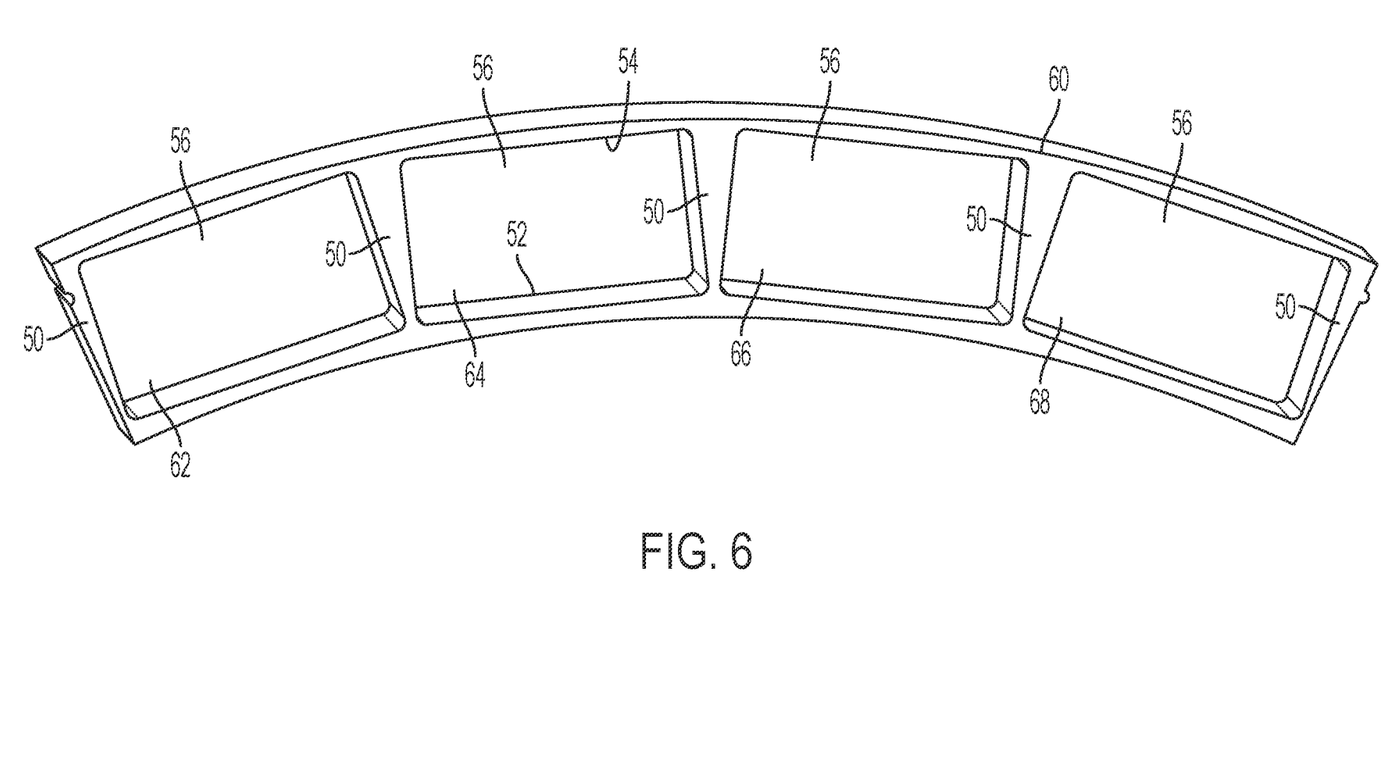
FIG. 6 depicts a segment of the gantry tube.

Referring to FIG. 6, a segment 60 of the gantry tube 44 is shown. In an embodiment, the segment 60 has a substantially curved shape and includes first 62, second 64, third 66 and fourth 68 channels. The gantry tube 44 may be formed by joining several segments 60. For example, the segments 60 may be joined on a mandrel using adhesives and mechanical locking features. In aspect of the invention, assembly of the segments 60 on a mandrel provides a uniform and repeatable surface for the RF screen 22 (see FIG. 8). In particular, the RF screen 22 is placed on the mandrel before the segments 60 are bonded together and to the RF screen 22.

The segment 60 may be fabricated using a polymer material and is formed by a pultrusion process that enables formation of thin walls suitable for forming the channels 56. It has been found by the inventors herein that the pultrusion technique may be used to form a segment 60 having a single channel 56 although the formation of additional channels 56, such as three or more channels 56, has been found to provide more suitable results. Further, a segment 60 that includes a channel 56 that is not desired may be removed by machining away the channel 56. For example, a single channel 56 may be machined away from a segment 60 having an odd number of channels 56. In an alternative method of fabrication, a large autoclave is used to join segments 60 that are made from pre-impregnated materials. The segments 60 are then cured under the vacuum and heat of the autoclave to form the gantry tube 44.

Figure 7A:
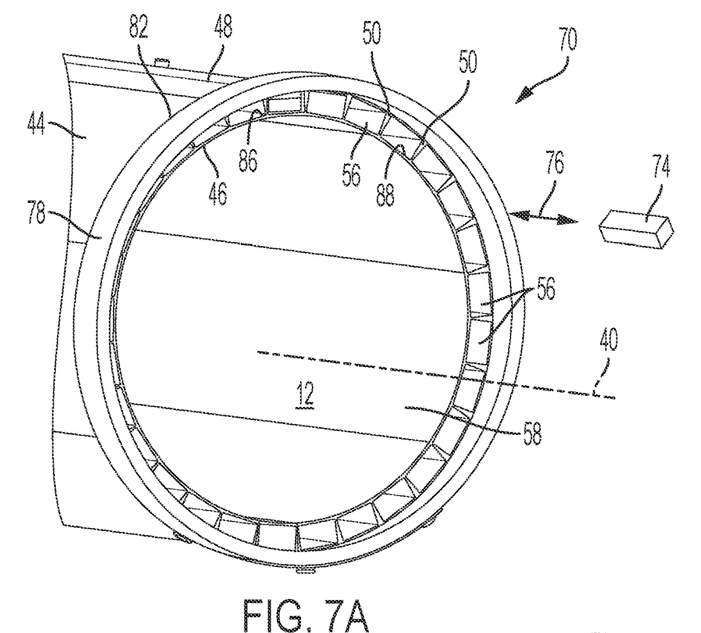
FIGS. 7A and 7B depict perspective patient and service end views of the gantry tube.
Figure 7B:
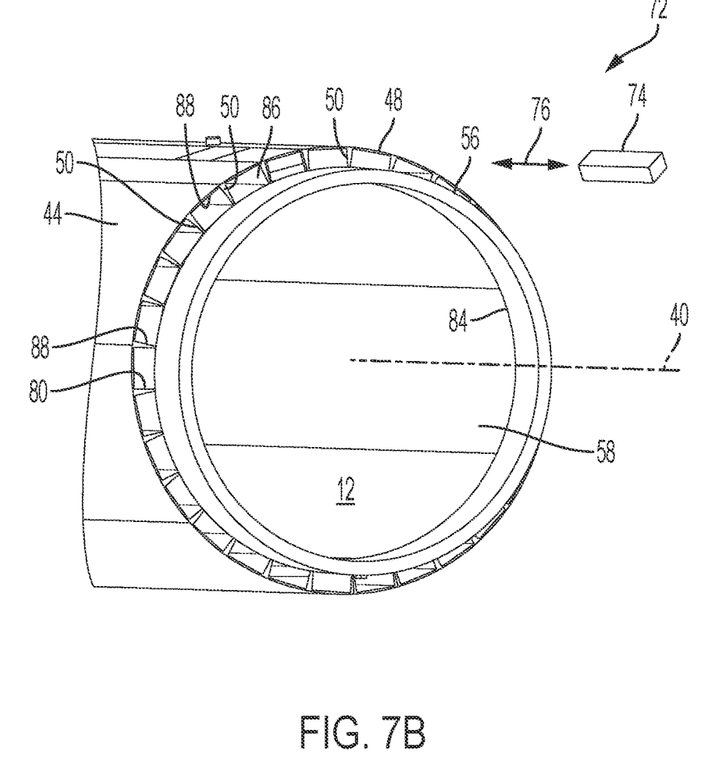
Figure 8:
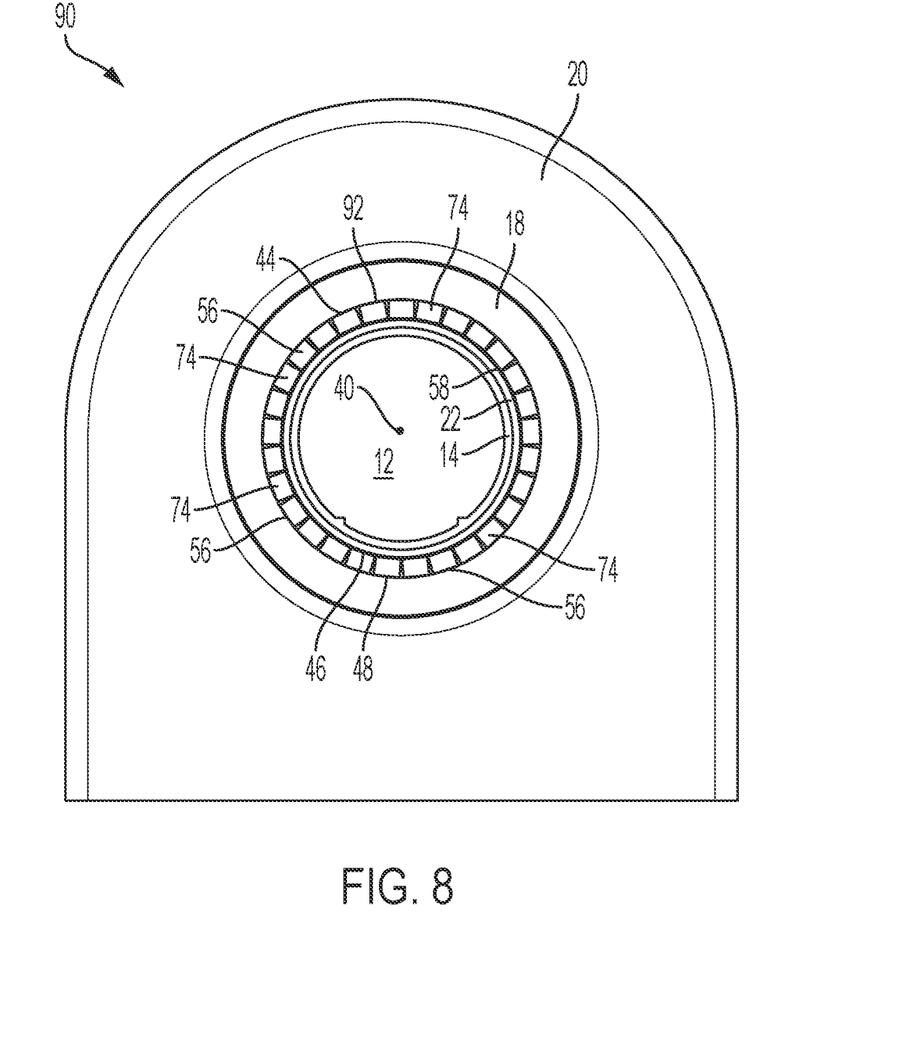
FIG. 8 is a front view of an MR/PET imaging system that includes the gantry tube of the invention.

Referring to FIGS. 7A and 7B, perspective patient 70 and service 72 end views of the gantry tube 44 are shown. The gantry tube 44 and channels 56 are oriented in a longitudinal direction about the longitudinal axis 40. In accordance with an aspect of the invention, the longitudinal orientation of each channel 56 enables insertion of a PET detector 74 (exemplary PET detector 74 is shown in FIGS. 7A and 7B) in each channel 56, or the removal of a PET detector 74 from a channel 56, in an axial direction (i.e., as shown by arrow 76) substantially parallel to the longitudinal axis 40. The gantry tube 44 is stationary and thus the PET detectors 74 are inserted or removed without moving or extending the gantry tube 44 relative to a remaining portion of the system 90.

A patient is received into the patient bore 12 via the patient end 70 (FIG. 7A). Servicing of the gantry tube 44 may be performed via the service end 72 (FIG. 7B) which is opposite the patient end 70. The channels 56 extend between the patient 70 and service 72 ends. In accordance with an aspect of the invention, each PET detector 74 may be inserted into an associated channel 56 in the axial direction 76 via the patient end 70 or the service end 72.

First 78 and second 80 support rings are located on the patient 70 and service 72 ends, respectively, of the gantry tube 44. The support rings 78, 80 may be removably attached to the gantry tube 44 and serve as an anchor point for the body coil 14 of the MRI portion of the system 90. In an embodiment, the first 78 and second 80 support rings are attached to an outer diameter 82 of the second tube 48 at the patient end 70 and an inner diameter 84 of the first tube 46 at the service end 72, respectively, of the gantry tube 44. This enables mounting of the gantry tube 44 inside the gradient coil 18 while still allowing access to the PET detectors 74 positioned in the channels 56 and shims that are used to adjust a position the gradient coil 18. Further, the support rings 78, 80 provide additional stiffness to the gantry tube 44.

The support rings 78, 80 are located outside of a field of view of the PET detectors 74 such that they do not attenuate a PET signal generated by the PET portion of the system 90. The support rings 78, 80 are optimally placed for mounting the gantry tube 44 to the system 90. In accordance with an aspect of the invention, the body coil 14, a component that is easily damaged in service, may be exchanged without removing the gantry tube 44.

Each segment 60 may be fabricated from a polymer enhanced with glass fiber such as glass reinforced plastic. Alternative materials having slight to moderate electrical conductivity, such as carbon fiber, polymers enhanced with copper or metallic additives and metallic meshes may be used to provide both structural strength and shielding against electromagnetic interference (EMI) generated during operation of the system 90. In particular, a balance must be achieved between providing proper shielding and the effects of eddy current heating on a conductive structure. In accordance with an aspect of the invention, a metallic surface 86 may be formed on an inside surface 88 of at least one channel 56 to form a waveguide. For example, the metallic surface 86 may be a metallic coating that is applied to the inside surface 88 or a metallic foil that is laminated on to the inside surface 88.

It has been found by the inventors herein that the pultrusion process produces segments 60 that are highly stable and precise. The geometry and reproducibility of the inner surface 58 of the first tube 46 is acceptable when a mandrel is used. A shape of an RF screen carrier should be precise and the inner surface of the segment 60 provides a suitable surface for the screen while adding no extra supporting features. Further, gaps between PET detectors 74 are minimized and the polymer profile in front of the PET detectors 74 has low attenuation. For example, the gaps may be approximately 1-3 mm in size.

Referring to FIG. 8, a front view of an MR/PET imaging system 90 is shown that includes the gantry tube 44 of the invention. The system 90 includes the patient bore 12 that receives a patient to be scanned, body coil 14, gantry tube 44 that forms a part of a PET gantry 92, gradient coil 18, superconducting magnet 20 and the RF screen 22 located on the first tube inner surface 58.

In an aspect of the invention, a gantry tube 44 for a system 90 is disclosed that enables insertion or removal of PET detectors 74 in and out of associated channels 56 of the gantry tube 44 by sliding the PET detectors 74 in and out of the associated channels 56 in an axial direction 76 at either the patient end 70 or service 72 end of the gantry tube 44. Access to the PET detectors 74 is provided without removing the gantry tube 44 from the magnet 20, thus reducing system downtime and the risk of damage to equipment. Since the gantry tube 44 does not move and remains inside the gradient coil 18, only a simple attachment to the magnet 20 is needed thus simplifying the mechanical structure of the system 90 (i.e., no rails, bearing, backplanes, etc. are needed). The risk of injury from moving a heavy gantry is substantially reduced and specialty tools are not required for performing service. In addition, the invention provides a known and reproducible surface to attach an RF shield of the body coil 14. Further, the RF cabin (i.e., a scan room wherein system 90 is located) may be optimized and reduced in size since the gantry tube 44 does not extend from the system 90 and thus an extended PET gantry length does not factor into room size requirements. In addition, the material used to fabricate the gantry tube 44 has low attenuation for the PET signal and gantry fabrication is very precise allowing for the accurate location of each PET detector 74 in the gantry tube 44.

In an alternative embodiment, the PET gantry 92 including gantry tube 44 may be integrated directly into the gradient coil 18. In this embodiment, the effects of vibration and heat on the PET detectors 74 should be minimized since both are detrimental to the associated electronics and operation of the PET detector 74.

Another embodiment would convolve the body coil 14 and PET gantry 92. In this embodiment, the PET detectors 74 reside within a radio frequency alternating field (B1) reflow space generated by the system 90 and would require significantly higher levels of EMI shielding. In addition, associated cabling may cause an antenna effect (due to currents on the cable shields). Further, shielded structures in this volume would be parasitic and require more power to offset the effect.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. A gantry tube for a medical imaging system, comprising:
   a first tube located within a second tube, wherein the first tube is oriented about a longitudinal axis of the system; and
   a plurality of wall elements that extend between the first and second tubes, wherein the walls and first and second tubes form a plurality of channels that extend in an axial direction substantially parallel to the longitudinal axis wherein each channel is configured to hold a detector of the system and wherein a detector is inserted into or removed from an associated channel in the axial direction and wherein the gantry tube is fabricated by joining a plurality of segments that each include sections of the first and second tubes, walls and a plurality of channels and wherein each segment is fabricated using a polymer enhanced with glass fiber.

2. The gantry tube according to claim 1, further including first and second support rings located at first and second ends of the gantry tube to provide additional stiffness to the gantry tube.

3. The gantry tube according to claim 1, wherein each segment includes first, second, third and fourth channels.

4. The gantry tube according to claim 1, wherein a width of each wall element increases as the wall extends from the first tube to the second tube to form a substantially wedge-shaped wall.

5. The gantry tube according to claim 1, wherein a detector is inserted into or removed from an associated channel without moving the gantry tube relative to the system.

6. The gantry tube according to claim 1, wherein the segments are formed by a pultrusion process.

7. A gantry tube for a medical imaging system, comprising:
   a first tube located within a second tube, wherein the first tube is oriented about a longitudinal axis of the system; and
   a plurality of wall elements that extend between the first and second tubes, wherein a width of each wall element increases as the wall extends from the first tube to the second tube to form a substantially wedge-shaped wall and wherein the walls and first and second tubes form a plurality of channels that extend in an axial direction substantially parallel to the longitudinal axis wherein each channel is configured to hold a detector of the system and wherein a detector is inserted into or removed from an associated channel in the axial direction from either a first end or a second end of the gantry tube and wherein the gantry tube is fabricated by joining a plurality of segments that each include sections of the first and second tubes, walls and a plurality of channels and wherein each segment is fabricated using a polymer enhanced with glass fiber.

8. The gantry tube according to claim 7, further including first and second support rings located at first and second ends of the gantry tube to provide additional stiffness to the gantry tube.

9. The gantry tube according to claim 7, wherein each segment includes first, second, third and fourth channels.

10. The gantry tube according to claim 7, wherein each channel has a substantially rectangular shape.

11. The gantry tube according to claim 7, wherein the imaging system is a magnetic resonance/positron emission tomography (MR/PET) imaging system and the detectors are PET detectors.

12. The gantry tube according to claim 7, wherein a detector is inserted into or removed from an associated channel without moving the gantry tube relative to the system.

13. The gantry tube according to claim 7, wherein the segments are formed by a pultrusion process.

14. A method of inserting a detector into a gantry tube of a medical imaging system or removing a detector from the gantry tube, comprising:
   providing a first tube located within a second tube, wherein the first tube is oriented about a longitudinal axis of the system;
   providing a plurality of wall elements that extend between the first and second tubes to form a plurality of channels wherein the channels extend in an axial direction substantially parallel to the longitudinal axis;
   joining a plurality of segments that each include sections of the first and second tubes, walls and a plurality of channels to form the gantry tube wherein each segment is fabricated using a polymer enhanced with glass fiber; and
   moving a detector in the axial direction to either insert the detector into an associated channel or remove a detector from an associated channel.

15. The method according to claim 14, further including providing first and second support rings located at first and second ends of the gantry tube to provide additional stiffness to the gantry tube.

16. The method according to claim 14, wherein each segment includes first, second, third and fourth channels.

17. The method according to claim 14, further including increasing a width of each wall element as the wall extends from the first tube to the second tube to form a substantially wedge-shaped wall.

18. The method according to claim 17, wherein each channel has a substantially rectangular shape.

19. The method according to claim 14, wherein a detector is inserted into or removed from an associated channel without moving the gantry tube relative to the system.

20. The method according to claim 14, wherein the segments are formed by a pultrusion process.

* * * * *